(12) United States Patent
Schneider et al.

(10) Patent No.: US 6,706,529 B2
(45) Date of Patent: *Mar. 16, 2004

(54) METHODS FOR SEQUENCING PROTEINS

(75) Inventors: Luke V. Schneider, Half Moon Bay, CA (US); Michael P. Hall, San Carlos, CA (US); Jeffrey N. Peterson, Foster City, CA (US)

(73) Assignee: Target Discovery, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/068,359

(22) Filed: Feb. 6, 2002

(65) Prior Publication Data

US 2002/0132357 A1 Sep. 19, 2002

Related U.S. Application Data

(62) Division of application No. 09/513,395, filed on Feb. 25, 2000, now Pat. No. 6,379,971.
(60) Provisional application No. 60/130,238, filed on Apr. 20, 1999.

(51) Int. Cl.$^7$ ............................................... G01N 33/00
(52) U.S. Cl. .................. 436/89; 436/173; 530/402; 530/412
(58) Field of Search .................. 436/89, 173; 530/402, 530/412

(56) References Cited

U.S. PATENT DOCUMENTS

| | | | |
|---|---|---|---|
| 4,830,010 A | 5/1989 | Marshall | |
| 4,842,701 A | 6/1989 | Smith et al. | 204/180.1 |
| 4,994,165 A | 2/1991 | Lee et al. | 204/299 R |
| 5,306,412 A | 4/1994 | Whitehouse et al. | 204/299 R |
| 5,386,832 A | 2/1995 | Wagner et al. | |
| 5,470,753 A | * 11/1995 | Sepetov et al. | 436/89 |
| 5,505,832 A | 4/1996 | Laukien et al. | 204/452 |
| 5,538,897 A | * 7/1996 | Yates, III et al. | 436/89 |
| 5,827,659 A | * 10/1998 | Patterson | 435/6 |
| 5,856,082 A | 1/1999 | Aebersold et al. | 435/4 |
| 5,872,010 A | 2/1999 | Karger et al. | 436/173 |
| 5,919,709 A | * 7/1999 | Parmelee et al. | 436/89 |
| 6,004,770 A | * 12/1999 | Nelson | 435/23 |
| 6,017,693 A | * 1/2000 | Yates, III et al. | 435/5 |
| 6,027,890 A | 2/2000 | Ness et al. | |
| 6,277,644 B1 | 8/2001 | Farnsworth et al. | 422/68.1 |
| 6,329,146 B1 | 12/2001 | Crooke et al. | 435/6 |
| 6,335,525 B1 | 1/2002 | Takada et al. | 250/288 |
| 6,379,971 B1 | 4/2002 | Schneider et al. | 436/173 |

FOREIGN PATENT DOCUMENTS

| | | |
|---|---|---|
| WO | WO 96/33406 A1 | 10/1996 |
| WO | WO 99/32501 A1 | 7/1999 |
| WO | WO 00/11208 A1 | 2/2000 |
| WO | WO 02/061661 A2 | 8/2002 |

OTHER PUBLICATIONS

Li, G. et al., "Improvement on sample handling for rapid mass spectrometric Identification of protesns resolved by 2D gel electrophoresis". Book of Abstracts, 213th ACS National Meeting, San Francisco, 13–17, Anal. 92 (Apr. 1997).
Mann and Wilm, "Error–Tolerant Identification of Peptides in Sequence Databases by Peptide Sequence Tags", *Anal. Chem.*, 66:(24) 4390–4399 (Dec. 15, 1994).
Jensen et al., "Sequence patterns produced by incomplete enzymatic digestion or one–step Edman degradation of peptide mixtures as probes for protein database searches", *Electrophoresis*, 17:938–944 (1996).
Wilkins et al., "Protein identification with sequence tags", *Current Biology*, 6(12):1543–1544 (1996).
Wilkins et al., "Rapid Protein Identification Using N–Terminal "Sequence Tag" and Amino Acid Analysis", *Biochemical and Biophysical Research Communications*, 221: 609–613, (1996) Article No. 0643.
Wilkins et al., "Protein Identification with N and C–Terminal Sequence Tags in Proteome Projects", *J. Mol. Biol.*, 278: 599–608 (1998).
Yates, J.R., *Anal. Biochem.*, 214:397–408 (1993).
Scholz, E., *J Capillary Electrophor*; 4:287–292 (1997).
Biemann, K., *Methods Enzymol.*, 193:455–79 (1990).
Schnoelzer, M., *Electrophoresis*, 17:945–953 (1996).
Zaia, J., *J. Am. Soc. Mass Spectrom.*, 6:428–36 (1995).
Stuits, J.T., *Anal. Chem.*, 65:1702–1708 (1993).
Zaia, J., *Methods Mol. Biol.*, 61:29–41 (1996).
Huehmer, A.F.R., *Anal. Chem.*, 69:29R–57R (1997).
Rose, K., *Biochem. J.*, 250:253–259 (1988).
Shevchenko, A., *Proc. Natl. Acad. Sci. U.S.A.*, 93:14440–14445 (1996).
Clauser, K.R., *Proc. Natl. Acad. Sci. U.S.A.*, 92:5072–5076 (1995).
Li, G., *Electrophoresis*, 18:391–402 (1997).
Murphy, C.M., *Anal. Chem.*, 67:1644–1645 (1995).
Johnson, R. S. et al., *International Journal of Mass Spectrom and Ion Process*, 86:137–154 (1998).
Vath, J.E. et al., *Fresenlus Z Anal. Chem.*, 331:248–252 (1998).
Wagner, D.S. et al., *Biol. Mass Spectrom.*, 20:419–425 (1991).
Huang, Z.–H. et al., *Anal. Biochem.*, 266:305–317 (1999).
Tomer, K.B. et al., *J. Am. Chem. Soc.*, 105:5487–5488 (1993).
Bures, E.J. et al., *Anal. Biochem.*, 224:364–372 (1995).
Aebersold, R. et al., *Protein Science*, pp. 494–503 (Cambridge University Press (1992).
Provisional Patent Application No. 60/415,481, filed Oct. 1, 2002.

(List continued on next page.)

*Primary Examiner*—Jill Warden
*Assistant Examiner*—Monique T. Cole
(74) *Attorney, Agent, or Firm*—Townsend and Townsend and Crew LLP

(57) ABSTRACT

The present invention provides a method for protein sequencing using mass spectrometry. Also provided are protein labeling agents and labeled proteins for use in conjunction with the present method.

10 Claims, No Drawings

OTHER PUBLICATIONS

Patent Application Ser. No. 10/068,359, filed Feb. 6, 2002, entitled: Method For Sequence Proteins.

Patent Application Ser. No. 10/035,349, filed Oct. 19, 2001, entitled: Mass Defect Labeling For The Determination Of Oligomer Sequences.

Provisional Patent Application No. 60/242,165, filed May 7, 2001.

Patent Application Ser. No. 09/513,907, filed Feb. 25, 2000, entitled: Polypeptide Fingerprinting Methods And Bioinformatics Data Base System.

Patent Application Ser. No. 09/551,937, filed Apr. 19, 2000, entitled: Labeling Of Protein Samples.

Provisional Patent Application No. 60/242,398.

* cited by examiner

METHODS FOR SEQUENCING PROTEINS

CROSS REFERENCES TO RELATED APPLICATIONS

This application is a division of Ser. No. 09/513,395 filed Feb. 25, 2000 now U.S. Pat. No. 6,379,971 which claims priority to U.S. Provisional Patent Application 60/130,238, filed on Apr. 20, 1999. This application is also related to 60/075,715, filed on Feb. 24, 1998. This application is also related to commonly assigned co-pending U.S. patent application Ser. No. 09/513,486, titled "Protein Separation via Multidimensional Electrophoresis," and filed on an even date herewith. This application is also related to commonly assigned co-pending U.S. patent application Ser. No. 09/513,907, titled "Polypeptide Fingerprinting Methods and Bioinformatics Database System," and filed on an even date herewith. Each of these patent applications is incorporated herein in their entirety for all purposes.

BACKGROUND OF THE INVENTION

Historically, techniques such as Edman degradation have been extensively used for protein sequencing. See, Stark, in: Methods in Enzymology, 25:103–120 (1972); Niall, in: Methods in Enzymology, 27:942–1011 (1973); Gray, in: Methods in Enzymology, 25:121–137 (1972); Schroeder, in: Methods in Enzymology, 25:138–143 (1972); Creighton, Proteins: Structures and Molecular Principles (W. H. Freeman, N.Y., 1984); Niederwieser, in: Methods in Enzymology, 25:60–99 (1972); and Thiede, et al. FEBS-Lett., 357:65–69 (1995). However, sequencing by collision-induced dissociation mass spectrometry (MS) methods (MS/MS sequencing) has rapidly evolved and has proved to be faster and require less protein than Edman techniques. See, Shevchenko, A., et al., Proc. Natl. Acad. Sci. (USA), 93:14440–14445 (1996); Wilm, et al., Nature, 379:466–469 (1996); Mark, J., "Protein structure and identification with MS/MS," paper presented at the PE/Sciex Seminar Series, Protein Characterization and Proteomics: Automated high throughput technologies for drug discovery, Foster City, Calif. (March, 1998); and Bieman, Methods in Enzymology, 193:455–479 (1990).

MS sequencing is accomplished either by using higher voltages in the ionization zone of the MS to randomly fragment a single peptide isolated from a protein digest, or more typically by tandem MS using collision-induced dissociation in the ion trap. See, Bieman, ibid. Several techniques can be used to select the peptide fragment used for MS/MS sequencing, including accumulation of the parent peptide fragment ion in the quadrapole MS unit (see, Mark, J. ibid.; Mann, M., paper presented at the IBC Proteomics conference, Boston, Mass. (Nov. 10–11, 1997); and Bieman, Methods in Enzymology, 193:455479 (1990)), capillary electrophoretic separation coupled to ES-TOF MS detection (see, Aebersold, R. "Proteome analysis: Biological assay or data archive?," paper presented at the IBC Proteomics conference, Coronado, Calif. (Jun. 11–12, 1998) and Smith, et al., in: CRC Handbook of Capillary Electrophoresis: A Practical Approach, Chp. 8, pgs 185–206 (CRC Press, Boca Raton, Fla., 1994)), or other liquid chromatographic separations (Niall, H. D., in: Methods in Enzymology, 27:942–1011 (1973) and Creighton, T. E., Proteins: Structures and Molecular Principles (W. H. Freeman, N.Y., 1984)). The amino acid sequence of the peptide is deduced from the molecular weight differences observed in the resulting MS fragmentation pattern of the peptide using the published masses associated with individual amino acid residues in the MS (Biemann, K., in: Methods in Enzymology., 193:888 (1990), and has been codified into a semi-autonomous peptide sequencing algorithm (Hines, et al., J Am Soc Mass Spectrom, 3:326–336 (1992)).

For example, in the mass spectrum of a 1425.7 Da peptide (HSDAVFTDNYTR) isolated in an MS/MS experiment acquired in positive ion mode, the difference between the full peptide 1425.7 Da and the next largest mass fragment ($y_{11}$, 1288.7 Da) is 137 Da. This corresponds to the expected mass of an N-terminal histidine residue that is cleaved at the amide bond. For this peptide, complete sequencing is possible as a result of the generation of high-abundance fragment ions that correspond to cleavage of the peptide at almost every residue along the peptide backbone. In the above-recited peptide sequence, the generation of an essentially complete set of positively-charged fragment ions that includes either end of the peptide is a result of the basicity of both the N- and C-terminal residues. When a basic residue is located at the N-terminus and/or C-terminus, most of the ions produced in the collision induced dissociation (CID) spectrum will contain that residue (see, Zaia, J., in: Protein and Peptide Analysis by Mass Spectrometry, J. R. Chapman, ed., pp. 29–41, Humane Press, Totowa, N.J. 1996; and Johnson, R. S., et al., Mass Spectrom. Ion Processes, 86:137–154 (1988)). since positive charge is generally localized at the basic site. The presence of a basic residue typically simplifies the resulting spectrum, since a basic site directs the fragmentation into a limited series of specific daughter ions. Peptides that lack basic residues tend to fragment into a more complex mixture of fragment ions that makes sequence determination more difficult.

Extending the concept of simplifying the CID spectrum of a peptide by including a charge concentrating moiety on either terminus of the peptide, others have demonstrated that attaching a hard positive charge to the N-terminus directs the production of a complete series of N-terminal fragment ions from a parent peptide in CID experiments regardless of the presence or absence of a basic residue at the N-terminus. See, Johnson, R. S., et al., Mass Spectrom. Ion Processes, 86:137–154 (1988); Vath, J. E., et al., Fresnius Zaia. Chem., 331:248–252 (1988); Stults, J. T., et al., Anal. Chem., 65:1703–1708 (1993); Zaia, J., et al., J. Am. Soc. Mass Spectrom., 6:423–436 (1995); Wagner, D. S., et al., Biol. Mass Spectrom., 20:419–425 (1991); and Huang, Z.-H., et al., Anal. Biochem., 268:305–317 (1999). Theoretically, all fragment ions are produced by charge-remote fragmentation that is directed by the fixed-charged group. See, Tomer, K. B., et al., J. Am. Chem. Soc., 105:5487–5488 (1983).

Peptides have been labeled with several classes of fixed-charge groups, including dimethylalkylammonium, substituted pyridinium, quaternary phosphonium, and sulfonium derivatives. Characteristics of useful labels include, ease of synthesis, increase in ionization efficiency of labeled peptides, and formation from a labeled peptide of a specific fragment ion series with minimal unfavorable label fragmentation. Zaia (in: Protein and Peptide Analysis by Mass Spectrometry, J. R. Chapman, ed., pp. 2941, Humana Press, Totowa, N.J., 1996) reported that the labels satisfying these criteria include those of the dimethylalkylammonium class and quarternary phosphonium derivatives. Moreover, it has been reported that substituted pyridinium derivatives are useful in high-energy CID. See, Bures, E. J., et al., Anal. Biochem., 224:364–372 (1995) and Aebersold, R., et al., in: Protein Science, pp. 494–503 (Cambridge University Press, 1992).

Despite some progress in analytical methodology, protein identification remains a major bottleneck in field of proteomics. For example, it can require up to 18 hours to generate a protein sequence tag of sufficient length to allow the identification of a single purified protein from its predicted genomic sequence. Shevchenko, A., et al., *Proc. Natl. Acad. Sci. (USA)*, 93:14440–14445 (1996). Moreover, although unambiguous protein identification can be attained by generating a protein sequence tag (PST, see Clauser, K. R., et al., *Proc. Natl. Acad. Sci. (USA)*, 92:5072–5076 (1995) and Li, G., M., et al., *Electrophoresis*, 18:391–402 (1997)), limitations on the ionization efficiency of larger peptides and proteins restrict the intrinsic detection sensitivity of MS techniques and inhibit the use of MS for the identification of low abundance proteins. Furthermore, limitations on the mass accuracy of time of flight (TOF) detectors can also constrain the usefulness of presently utilized methods of MS/MS sequencing, requiring that proteins be digested by proteolytic and/or chemolytic means into more manageable peptides (see Ambler, R. P., in: *Methods in Enzymology*, 25:143–154 (1972) and Gross, E., in: *Methods in Enzymol.*, 11:238–255 (1967) prior to sequencing.

Two basic strategies have been proposed for the MS identification of proteins after their separation from a protein mixture: 1) mass profile fingerprinting ('MS fingerprinting') (see, James, P., et al., *Biochem. Biophys. Res. Commun.*, 195:58–64 (1993) and Yates, J. R., et al., *Anal. Biochem.*, 214:397–408 (1993)); and 2) sequencing of one or more peptide domains by MS/MS ('MS/MS sequencing')(see Mann, M., paper presented at the IBC Proteomics conference, Boston, Mass. (Nov. 10–11, 1997); Wilm, M., et al., *Nature*, 379:466–469 (1996); and Chait, B. T, et al., *Science*, 262:89–92 (1993)). MS fingerprinting is achieved by accurately measuring the masses of several peptides generated by a proteolytic digest of the intact protein and searching a database for a known protein with that peptide mass fingerprint. MS/MS sequencing involves actual determination of one or more PSTs of the protein by generation of sequence-specific fragmentation ions in the quadrapole of an MS/MS instrument.

Clauser et al., *Proc. Natl. Acad. Sci. (USA)*, 92:5072–5076 (1995) have suggested that proteins can only be unambiguously identified through the determination of PSTs that allow reference to the theoretical sequences determined from genomic databases. Li et al., *Electrophoresis*, 18:391–402 (1997) appear to have proven this assertion by finding that the reliable identification of individual proteins by MS fingerprinting degenerated as the size of the comparative theoretical peptide mass database increased. Li et al., ibid., also reported that they were only able to obtain peptide maps for the highest abundance proteins in the gel because of sensitivity limitations of the MS, even though their matrix assisted laser desorption MALDI methodology was demonstrated to improve the detection sensitivity over previously reported methods. Clearly, rapid and cost effective protein sequencing techniques will improve the speed and lower the cost of proteomics research.

The present invention provides such methods.

SUMMARY OF THE INVENTION

The present invention overcomes many of the difficulties associated with current MS-based protein sequencing technologies, including, for example, ionization inefficiency and inaccuracies in fragment mass. Because the methods of the invention preferably eliminate the need for proteolytic or chemolytic digestion of the protein, the present methods provide protein sequencing times that are significantly reduced from the times obtainable using prior methods. Moreover, because the proteins being sequenced are highly fragmented using the present methods, the ionization efficiency and the volatility of the resulting fragments are higher than those of the parent protein, thus leading to a detection sensitivity that is improved over prior methods.

Thus, in one aspect, the present invention provides a method for sequencing a portion of a protein, comprising:
(a) contacting a protein with a C-terminus or N-terminus labeling moiety to covalently attach a label to the C- or N-terminus of the protein and form a labeled protein; and
(b) analyzing the labeled protein using a mass spectrometric fragmentation method to determine the sequence of at least the two C-terminus or two N-terminus residues.

In one group of embodiments, the method further comprises:
(c) identifying the protein by using the sequence of the at least two C-terminus or two N-terminus residues to search predicted protein sequences from a database of gene sequence data.

In another aspect, the present invention provides a method for sequencing a portion of a protein in a protein mixture, the method comprising:
(a) contacting the protein mixture with a C-terminus or N-terminus labeling moiety to covalently attach a label to the C- or N-terminus of the protein and form a labeled protein mixture;
(b) separating individual labeled proteins in the labeled protein mixture; and
(c) analyzing the labeled proteins from step (b) by a mass spectrometric method to determine the sequence of at least two C-terminus or two N-terminus residues.

In one group of embodiments, the method further comprises:
(d) identifying the protein by using the sequence of at least two C-terminus or two N-terminus residues in combination with a separation coordinate of the labeled protein and the protein terminus location of the sequence to search predicted protein sequences from a database of gene sequence data.

In each of the methods above, the use of nonproteolytic protein sequencing by in-source fragmentation provides advantages over conventional MS/MS sequencing approaches. One particular advantage is time savings due to elimination of protein digestion steps and elimination of the need to accumulate low volatility peptide ions in the quadrapole. Another advantage is that fewer sequence ambiguities result due to the improved absolute mass accuracy gained by working at the low end of the mass spectrum. Another advantage is that better ionization efficiency and corresponding detection sensitivity result from using more energetic ionization conditions and the introduction of a hard or ionizable charge on the fragments through the addition of the label. Yet another advantage of introducing a charge through the label is the ability to determine partial protein sequences from regions of a protein that may not contain ionizable amino acid residues.

Finally, this method provides a contiguous protein sequence tag (PST) that can be used both for unambiguous protein identification or to generate an N- or C-terminal nucleic acid probe useful for isolating the corresponding cDNA from native cell or tissue samples.

BRIEF DESCRIPTION OF THE DRAWINGS

FIG. 1 is the minimally fragmenting 12 V spectrum of glycogen phosphorylase A protein. A zero charge mass deconvolution of the multiply charged mass peaks observed between 700 and 4000 amu was prepared using the BioSpec Data Explorer™ software.

FIG. 2 is a graphical display of the increase in relative abundance for peaks corresponding to the acetylated peptide masses, with increasing nozzle potential.

FIG. 3 is an example of a substanitally fragmented mass spectrum, corresponding to 250 V nozzle potential for glycogen phosphorylase A.

FIG. 4 is the minimally fragmenting 12 V spectrum of PITC-Bradykinin peptide.

FIG. 5 is a graphical display of the increase in relative abundance for peaks corresponding to the PITC-labeled peptide masses, with increasing nozzle potential.

FIG. 6 is an example of a substantially fragmented mass spectrum, corresponding to 250 V nozzle potential for PITC-labeled Bradykinin.

FIG. 7 is a graphical display of the peak counts corresponding to the a-ions generated from the IMB-labeled peptide fragment masses that were clearly observed to increase in relative abundance with increasing nozzle potential with a maximum fragmentation abundance noted at about 200V.

FIG. 8 is a graphical display of the peak counts corresponding to the b-ions generated from the IMB-labeled peptide fragment masses that were clearly observed to increase in relative abundance with increasing nozzle potential with a maximum fragmentation abundance noted at about 200V.

FIG. 9 is a mass spectrum from SPITC-labeled apomyoglobin obtained in the negative ion mode. The nozzle potential was increased from a minimum setting of 125 V to a maximum of 300V in 25–50 V increments with 1 minute of instrument equilibration time alotted before collecting spectra at each nozzle potential. A total of thirty 3-second spectra were accumulated for analysis at each nozzle potential.

FIG. 10 is a graphical display of the increase in relative abundance for the $b_1$, $a_2$, $b_2$, $a_3$, and $b_3$ ions occurring above nozzle potentials of 250V.

FIG. 11 shows the increase in relative abundance for the doubly charged $Y_{1-8}$ ions generated from the C-terminal (2-aminoethyl)trimethylammonium-labeled Bradykinin peptide obtained in positive ion mode. The nozzle potential was increased from a minimum of 50 V to a maximum of 300 V in 50 V increments with 1 minute of instrument equilibration time alotted before collecting spectra at each nozzle potential. A total of sixty 3-second spectra were accumulated for analysis at each nozzle potential.

DETAILED DESCRIPTION OF THE INVENTION AND THE PREFERRED EMBODIMENTS

Definitions

Unless defined otherwise, all technical and scientific terms used herein generally have the same meaning as commonly understood by one of ordinary skill in the art to which this invention belongs. Generally, the nomenclature used herein and the laboratory procedures in molecular biology, organic chemistry and protein chemistry described below are those well known and commonly employed in the art. Standard techniques are used for peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document The nomenclature used herein and the laboratory procedures in analytical chemistry, and organic synthesis described below are those known and employed in the art. Standard techniques, or modifications thereof, are used for chemical syntheses and chemical analyses.

As used herein, the terms protein, peptide and polypeptide refer to a polymer of amino acid residues. The terms also apply to amino acid polymers in which one or more amino acids are chemical analogues of corresponding naturally-occurring amino acids, including amino acids which are modified by post-translational processes (e.g., glycosylation and phosphorylation).

"Protein", as used herein, means any protein, including, but not limited to peptides, enzymes, glycoproteins, hormones, receptors, antigens, antibodies, growth factors, etc., without limitation. Presently preferred proteins include those comprised of at least 25 amino acid residues, more preferably at least 35 amino acid residues and still more preferably at least 50 amino acid residues.

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. The amino acids may be either the D- or L-isomer. The L-isomers are generally preferred. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

"Protein sequencing tag," as used herein, refers to a contiguous series of at least two amino acids representing a partial sequence of a protein. A preferred PST includes a label of the invention or a fragment of a label of the invention or an ionized derivative of a label of the invention.

The term "alkyl" is used herein to refer to a branched or unbranched, saturated or unsaturated, monovalent hydrocarbon radical, generally having from about 1–30 carbons and preferably, from 4–20 carbons and more preferably from 6–18 carbons. When the alkyl group has from 1–6 carbon atoms, it is referred to as a "lower alkyl." Suitable alkyl radicals include, for example, structures containing one or more methylene, methine and/or methyne groups. Branched structures have a branching motif similar to i-propyl, t-butyl, i-butyl, 2-ethylpropyl, etc. As used herein, the term encompasses "substituted alkyls," and "cyclic alkyl."

"Substituted alkyl" refers to alkyl as just described including one or more substituents such as, for example, lower alkyl, aryl, acyl, halogen (i.e., alkylhalos, e.g., $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl moiety. Additionally, these groups may be pendent from, or integral to, the alkyl chain.

The term "aryl" is used herein to refer to an aromatic substituent, which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl" and "substituted aryl."

"Substituted aryl" refers to aryl as just described including one or more functional groups such as lower alkyl, acyl, halogen, alkylhalos (e.g. $CF_3$), hydroxy, amino, alkoxy, alkylamino, acylamino, acyloxy, phenoxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

The term "arylalkyl" is used herein to refer to a subset of "aryl" in which the aryl group is attached to another group by an alkyl group as defined herein.

"Substituted arylalkyl" defines a subset of "substituted aryl" wherein the substituted aryl group is attached to another group by an alkyl group as defines herein.

The term "acyl" is used to describe a ketone substituent, —C(O)R, where R is alkyl or substituted alkyl, aryl or substituted aryl as defined herein.

The term "halogen" is used herein to refer to fluorine, bromine, chlorine and iodine atoms.

The term "hydroxy" is used herein to refer to the group —OH.

The term "amino" is used to designate —NRR', wherein R and R' are independently H, alkyl, aryl or substituted analogues thereof. "Amino" encompasses "alkylamino" denoting secondary and tertiary amines and "acylamino" describing the group RC(O)NR'.

The term "alkoxy" is used herein to refer to the —OR group, where R is alkyl, or a substituted analogue thereof. Suitable alkoxy radicals include, for example, methoxy, ethoxy, t-butoxy, etc.

As used herein, the term "aryloxy" denotes aromatic groups that are linked to another group directly through an oxygen atom. This term encompasses "substituted aryloxy" moieties in which the aromatic group is substituted as described above for "substituted aryl." Exemplary aryloxy moieties include phenoxy, substituted phenoxy, benzyloxy, phenethyloxy, etc.

As used herein "aryloxyalkyl" defines aromatic groups attached, through an oxygen atom to an alkyl group, as defines herein. The term "aryloxyalkyl" encompasses "substituted aryloxyalkyl" moieties in which the aromatic group is substituted as described for "substituted aryl."

As used herein, the term "mercapto" defines moieties of the general structure —S—R wherein R is H, alkyl, aryl or heterocyclic as described herein.

The term "saturated cyclic hydrocarbon" denotes groups such as the cyclopropyl, cyclobutyl, cyclopentyl, etc., and substituted analogues of these structures. These cyclic hydrocarbons can be single- or multi-ring structures.

The term "unsaturated cyclic hydrocarbon" is used to describe a monovalent non-aromatic group with at least one double bond, such as cyclopentene, cyclohexene, etc. and substituted analogues thereof. These cyclic hydrocarbons can be single- or multi-ring structures.

The term "heteroaryl" as used herein refers to aromatic rings in which one or more carbon atoms of the aromatic ring(s) are replaced by a heteroatom such as nitrogen, oxygen or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "heteroaryl" wherein an alkyl group, as defines herein, links the heteroaryl group to another group.

"Substituted heteroaryl" refers to heteroaryl as just described wherein the heteroaryl nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defines by the term "substituted heteroaryl."

"Substituted heteroarylalkyl" refers to a subset of "substituted heteroaryl" as described above in which an alkyl group, as defined herein, links the heteroaryl group to another group.

The term "heterocyclic" is used herein to describe a monovalent saturated or unsaturated non-aromatic group having a single ring or multiple condensed rings from 1–12 carbon atoms and from 1–4 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc.

The term "heterocyclicalkyl" defines a subset of "heterocyclic" wherein an alkyl group, as defined herein, links the heterocyclic group to another group.

General

The present invention resides in a mass spectrometric method for protein sequencing, which is preferably nonproteolytic and nonchemolytic. The present method is practiced by labeling the N- or C-terminus of an intact protein with a unique mass tag, fragmenting the intact labeled protein in the ionization zone of a mass spectrometer (e.g., in-source fragmentation) and determining the sequence from the mass ladder of the resulting labeled peptide series. Labeled peptides are differentiated from unlabeled peptides by their unique mass signature in the resulting mass spectrum. In some embodiments, this process is accomplished in less than 1 min for a purified labeled protein, yielding a 500 to 1000-fold more rapid method than current MS/MS protein sequencing techniques.

The labeled proteins are highly fragmented in the ionization zone of the MS, in a manner that is preferably influenced by the presence of the label. Preferred labels lead to increased ionization efficiency and enhanced volatility of the resulting labeled peptide fragment ions, relative to the parent protein, thus improving the overall detection sensitivity. The sequence of the protein or protein sequence tag is preferably constructed from the low molecular weight end of the mass spectrum, providing advantages over prior methods, such as greater absolute mass accuracy and more facile sequencing, including resolution of Q and K residues, from the resulting labeled peptide fragments.

The selection of an appropriate label for this technique requires consideration of several criteria. First, the label is preferably robust enough to survive the fragmentation conditions of the MS. Second, the label preferably also creates a unique mass/charge (m/z) signature that is distinguishable from any unlabeled peptides generated from internal scissions of the protein backbone. Third, the label may also carry an ionizable or permanently ionized group to ensure that fragmentation produces high-abundance ions that include even uncharged N- and C-terminal residues.

Example 1 using glycogen phosphorylase, carrying a natural N-terminal acetylation label, illustrates the generality of the technique.

Description of the Embodiments

In one aspect, the present invention provides a method for sequencing a portion of a protein, comprising:

(a) contacting a protein with a C-terminus or N-terminus labeling moiety to covalently attach a label to the C- or N-terminus of the protein and form a labeled protein; and (b) analyzing the labeled protein using a mass spectrometric fragmentation method to determine the sequence of at least the two C-terminus or two N-terminus residues.

In this aspect of the invention the protein can be obtained from essentially any source. Preferably, the protein is isolated and purified to be free of interfering components. The isolated protein can be contacted with a C-terminus or N-terminus labeling moiety to covalently attach a label to the C- or N-terminus of the protein to form a labeled protein, suitable for analysis by mass spectrometric fragmentation methods.

Labeled Proteins

The labeling of proteins with various agents in an aqueous or mixed aqueous/organic solvent milieu is known in the art and a wide range of labeling reagents and techniques useful in practicing the present invention are readily available to those of skill in the art. See, for example, Means et al., CHEMICAL MODIFICATION OF PROTEINS, Holden-Day, San Francisco, 1971; Feeney et al., MODIFICATION OF PROTEINS: FOOD, NUTRITIONAL AND PHARMACOLOGICAL ASPECTS, Advances in Chemistry Series, Vol. 198, American Chemical Society, Washington, D.C., 1982; Feeney et al., FOOD PROTEINS: IMPROVEMENT THROUGH CHEMICAL AND ENZYMATIC MODIFICATION, Advances in Chemistry Series, Vol. 160, American Chemical Society, Washington, D.C., 1977; and Hermanson, BIOCONJUGATE TECHNIQUES, Academic Press, San Diego, 1996.

Labeling can be conducted and PSTs determined from either the N- or C-terminal end of the protein. About 59–90% of eukaryotic proteins are N-terminal acetylated (see, Creighton, T. E., Proteins: Structures and Molecular Principles (W. H. Freeman, N.Y., 1984) and are thus refractory to N-terminus labeling. However, the natural N-acetyl group of such proteins can sometimes be used as a label for purposes of this invention, but only where one or more of the amino acids within 4 residues of the N-terminus is ionizable (e.g., is a lysine, arginine, histidine, aspartic acid, or glutamic acid residue) or can be derivatized to be ionizable (e.g., tyrosine, serine, and cysteine residues). Accordingly, strategies to label either the N- or C-termini are provided to afford the greatest degree of sequencing ability for any given protein. Once a label is selected, a deconvolution algorithm can be modified to search for masses that correspond to any modified residues.

Labels

As noted above, the following considerations are relevant to the selection of a labeling agent:

i) the mass of the label is preferably unique and preferably shifts the fragment masses to regions of the spectrum with low background;

ii) the label preferably contains fixed positive or negative charges to direct remote charge fragmentation at the N- or C-terminus;

iii) the label is preferably robust under the fragmentation conditions and does not undergo unfavorable fragmentation;

iv) the labeling chemistry is preferably efficient under a range of conditions, particularly denaturing conditions, thereby reproducibly and uniformly labeling the N- or C-terminus;

v) the labeled protein preferably remains soluble in the MS buffer system of choice; and vi) the label preferably increases the ionization efficiency of the protein, or at least does not suppress it;

vii) the label may contain a mixture of two or more isotopically distinct species to generate a unique mass spectrometric pattern at each labeled fragment position.

In view of the label selection criteria, preferred labeling moieties are those that have a detection enhancement component, an ion mass signature component and a C-terminus or N-terminus reactive functional group. The reactive group can be directly attached to either or both of the other two label components.

In another embodiment, the reactive functional group is separated from one or both of the detection enhancement component and the ion mass signature component by a linker. The linker is preferably designed such that it is chemically stable and inert, and such that it allows efficient separation of the reactive group and at least one of the other two components of the tag Within a preferred embodiment of the invention, the linker is composed of a hydrocarbon chain or, most preferably, of a hydrocarbon chain linked to an aryl or heteroaryl ring and preferably provides additional separation between the ionizable group and the isothiocyanate group.

As will be understood by one of ordinary skill in the art, a virtually limitless array of hydrocarbon chains and modified hydrocarbon chains may be utilized within the present invention. Preferred hydrocarbon chains which are attached to the phenyl ring may be found in the family of alkanes, with particularly preferred linkers ranging from 2 carbon atoms to about 20 carbon atoms in length. Within a preferred embodiment of the invention, the linker is a phenethyl group.

Detection Enhancement Components

A detection enhancement component, as used herein, refers to a portion of the labeling moiety that facilitates detection of the protein fragments in the mass spectrometer. Accordingly, the detection enhancement component can provide a positively charged ionic species under fragmentation conditions in a mass spectrometer ionization chamber, or the component can provide a negatively charged ionic species under fragmentation conditions in a mass spectrometer ionization chamber. For many of the detection enhancement components, the amount of ionized species present will depend on the medium used to solubilize the protein. Preferred detection enhancement components (i.e., species that can generate a positive or negative charge) can be classified into three categories: 1) components that carry "hard" charge, 2) components that carry "soft" charge, and 3) components that provide no charge but are in close proximity to protein residues that carry "soft" charge.

Components that carry "hard" charge are arrangements of atoms that are ionized under all conditions, regardless of medium pH. "Hard" positively-charged detection enhancement components include, but are not limited to, tetraalkyl or tetraaryl ammonium groups, tetraalkyl or tetraaryl phosphonium groups, and N-alkylated or N-acylated heterocyclyl and heteroaryl (e.g., pyridinium) groups. "Hard" negatively-charged detection components include, but are not limited to, tetraalkyl or tetraacyl borate groups.

Components that carry "soft" charge are arrangements of atoms that are ionized at a specific pH, respectively (i.e., bases and acids). Within the context of the current invention, "soft" positive charges include those bases with a pKa of greater than 8, preferably greater than 10, and most preferably greater than 12. Within the context of the current invention, "soft" negative charges include those acids with a pKa of less than 4.5, and preferably less than 2, and most preferably less than 1. At the extremes of pKa, the "soft" charges approach classification as "hard" charges. "Soft" positively-charged detection enhancement components include, but are not limited to, 1°, 2°, and 3° alkyl or aryl ammonium groups, substituted and unsubstituted heterocyclyl and heteroaryl (e.g., pyridinium) groups, alkyl or aryl Schiff base or imine groups, and guanidino groups. "Soft" negatively-charged detection enhancement components include, but are not limited to, alkyl or aryl carboxylate groups, alkyl or aryl sulfonate groups, and alkyl or aryl phosphonate or phosphate groups.

For both "hard" and "soft" charged groups, as will be understood by one of ordinary skill in the art, the groups will be accompanied by counterions of opposite charge. For example, within various embodiments, the counterions for positively-charged groups include oxyanions of lower alkyl organic acids (e.g., acetate), halogenated organic acids (e.g., trifluoroacetate), and organosulfonates (e.g., N-morpholinoethane sulfonate). The counterions for negatively-charged groups include, for example, ammonium cations, alkyl or aryl ammonium cations, and alkyl or aryl sulfonium cations.

Components that are neutral but are in close proximity to protein residues that carry "soft" charge (e.g., lysine, histidine, arginine, glutamic acid, or aspartic acid) can be used as detection enhancement components. In this case, the label carries no ionized or ionizable groups, and the detection enhancement is provided by a nearby protein residue that carries charge. Within the context of the present invention, close proximity is defined as within about 4 residues from the labeled terminus of the protein, and more preferably within about 2 residues of the labeled terminus of the protein.

The detection enhancement component of the label can also be multiply charged or capable of becoming multiply charged. For example, a label with multiple negative charges can incorporate one or more singly charged species (e.g., carboxylate) or it can incorporate one or more multiply charged species (e.g., phosphate). In a representative example of this embodiment of the invention a species bearing multiple carboxylates, such as, for example a polyaminocarboxylate chelating agent (e.g., EDTP, DTPA) is attached to the protein. Methods of attaching polyaminocarboxylates to proteins and other species are well known in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, et al., Eds., American Chemical Society, Washington, D.C., 1982, pp. 370–387; Kasina et al., *Bioconjugate Chem.*, 9: 108–117 (1998); Song et al., *Bioconjugate Chem.*, 8: 249–255 (1997).

In a similar manner, labels having multiple positive charges can be purchased or prepared using methods accessible to those of skill in the art. For example, a labeling moiety bearing two positive charges can be rapidly and easily prepared from a diamine (e.g., ethylenediamine). In a representative synthetic route, the diamine is monoprotected using methods known in the art and the non-protected amine moiety is subsequently dialkylated with a species bearing one or more positive charges (e.g., (2-bromoethyl) trimethylammonium bromide) (Aldrich)). Deprotection using art-recognized methods provides a reactive labeling species bearing at least two positive charges. Many such simple synthetic routes to multiply charged labeling species will be apparent to one of skill in the art.

Ion Mass Signature Component

The ion mass signature component is the portion of the labeling moiety which preferably exhibits a unique ion mass signature in mass spectrometric analyses. The sum of the masses of the constituent atoms of the label is preferably uniquely different than the fragments of all the possible amino acids. As a result, the labeled amino acids and peptides are readily distinguished from unlabeled amino acids and peptides by their ion/mass pattern in the resulting mass spectrum. In a preferred embodiment, the ion mass signature component imparts a mass to a protein fragment produced during mass spectrometric fragmentation that does not match the residue mass for any of the 20 natural amino acids.

As will be understood by one of skill in the art, spurious mass spectral peaks can arise not only from the fragmentation of unlabeled amino acids and peptides but also from impurities in the sample and/or matrix. In order to further increase the uniqueness of the ion mass signature of the label and to be able to identify desired labeled fragment peaks amongst this "noise," it is preferable to shift the labeled fragments to regions of less spectral noise by optimizing the mass of the label. For example, it is preferred that the label mass generate an ion greater than 100 amu and less than 700 amu. This may be done by increasing the molecular weight of a low molecular weight label or by increasing the number of charges on a high molecular weight label.

An alternative method for providing a more unique mass signature to a labeling moiety is to incorporate stable isotopes in the label (see, for example, Gygi et al., *Nature Biotechnol.* 17: 994–999 (1999)). For example, by incorporating eight deuterium atoms into a labeling moiety and labeling the protein with a 50:50 mixture of the deuterated and nondeuterated label, the resulting singly-charged fragments that include the label are easily identified as equally intense doublets; one at the mass corresponding to the species with the nondeuterated label and the other at the mass corresponding to the species with the deuterated label with a spacing of 8 amu. In a preferred embodiment, the mass difference is more than about 1 amu at the single charge state. In the most preferred embodiment the mass difference is from about 4 to about 10 amu at the single charge state.

Another method for providing a more unique mass signature to a labeling moiety is to incorporate a mixture of alkyl and/or aryl substitutions onto the label, such that the corresponding set of fragment peaks is easily recognizable in the mass spectrum. For example, the protein can be labeled with a mixture of a label that contains a trimethyl ammonium group and the same label that contains a dimethylethylammonium group in place of the trimethyl ammonium group. This labeling moiety produces two fragment ion peaks for each amino acid in the sequence that differ by 14 amu from each other. It will be apparent to those skilled in the art that many such combinations can be derived.

Reactive Groups

A third component of the labeling moiety is a functional group which is reactive with the N-terminus amino group, the C-terminus amino group or another constituent of the N- or C-terminus amino acid.

The reactive functional group can be located at any position on the tag. For example, the reactive group can be located on an aryl nucleus or on a chain, such as an alkyl chain, attached to an aryl nucleus. When the reactive group is attached to an alkyl, or substituted alkyl chain tethered to an aryl nucleus, the reactive group is preferably located at a terminal position of an alkyl chain. Reactive groups and classes of reactions useful in practicing the present invention are generally those that are well known in the art of bioconjugate chemistry. Currently favored classes of reactions are those which proceed under relatively mild conditions in an aqueous or mixed aqueous/organic solvent milieu.

Particularly preferred chemistries that target the primary amino groups in proteins (including the N-terminus) include, for example: aryl fluorides (see, Sanger, F., *Biochem. J.*, 39:507 (1945); Creighton, T. E., *Proteins: Structures and Molecular Principles* (W. H. Freeman, N.Y., 1984); Niederwieser, A., in: *Methods in Enzymology*, 25:60–99 (1972); and Hirs, C. H. W., et al., *Arch. Biochem. Biophys.*, 111:209–222 (1965), sulfonyl chlorides (Gray, W. R., in: *Methods in Enzymology*, 25:121–137 (1972)), cyanates (Stark, G. R., in: *Methods in Enzymology*, 25:103–120 (1972)), isothiocyanates (Niall, H. D., in: *Methods in Enzymology*, 27:942–1011 (1973)), immidoesters (Galella, G., et al., *Can. J. Biochem.*, 60:71–80 (1982)), N-hydroxysuccinimidyl esters (Lomant, A. J., et al., *J. Mol. Biol.*, 104:243–261 (1976)), 0-acylisoureas (Lomant, A. J., et al., *J Mol. Biol.*, 104:243–261 (1976)), chlorocarbonates and carbonylazides (Solomons, T.W.G, Organic Chemistry (John Wiley & Sons, N.Y., 1976), aldehydes (Novotny et al., *Anal. Chem.*, 63:408 (1991) and Novotny et al., *J. Chromatography*, 499:579 (1990)), and alkylhalides and activated alkenes (Wagner, D. S., et al., *Biol Mass Spectrometry*, 20:419425 (1991)). Preferred examples of chemical constituents that react with the carboxyl groups of proteins are benzyl halides (Solomons, T.W.G, Organic Chemistry (John Wiley & Sons, N.Y., 1976); Merrifield, B., *Science*, 232:341–347 (1986); and Horton, H. R., et al., *Methods in Enzymology*, 25:468 (1972)) and carbodiimide (Yamada, H., et al., *Biochem.*, 20:4836–4842)), particularly if stabilized using N-hydroxysuccinimide (see, Grabarek, Z., et al., *Anal. Biochem.* 185:131–135 (1990)). Both of these carboxyl labeling approaches are expected to label carboxyl containing amino acid residues (e.g., aspartate and glutamate) along with that of the C-terminus. These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

The reactive functional groups can be chosen such that they do not participate in, or interfere with, the reactions necessary to assemble the tag. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Table 1 provides a non-limiting list of a number of labeling moieties useful in the labels of the present invention.

TABLE 1

| Label | Source | Linkage Formed |
|---|---|---|
| Amine Labeling | | |
| 2,4,6-trinitrobenzenesulfonic acid | Aldrich | Aryl amine |
| Lissamine ™ rhodamine B sulfonyl chloride | Molecular Probes | Sulfonamide |
| 2′,7′-dichlorofluoroscein-5-isothiocyanate | Molecular Probes | Thiourea |
| 4,4-difluoro-5,7-dimethyl-4-bora-3a,4a-diaza-s-indacene-3-propionic acid, sulfosuccinimidyl ester | Molecular Probes | Amide |
| Nahthalene-2,3-dicarboxylaldehyde | Molecular Probes | Isoindole |
| Carboxyl Labeling | | |
| 5-(bromomethyl)fluorescein | Molecular Probes | Ester |
| N-cyclohexyl-N′-(4-(dimethylamino) naphthyl)carbodiimide | Molecular Probes | N-Acylurea |
| 1-ethyl-3-(3-dimethylaminopropyl)-carbodiimide hydrochloride with N-hydroxysuccinimide and 5-aminofluorescein | Pierce Aldrich Molecular Probes | Amide |

One of skill in the art will understand that labeling techniques are readily available for a number of the labeling moieties. An example of an N-terminus labeling group (dansyl chloride) and a C-terminus labeling group (carbodiimide) are provided as illustrative of the invention, with references to a more complete description of their use. The focus on these two labeling moieties is for clarity of illustration and does not limit the scope of the invention.

Dansyl chloride undergoes a nucleophilic attack by the amines in proteins at alkaline pH, producing an aromatic sulfonamide. Sulfonyl chlorides, however, depending on the pH, can also react with secondary amines. The aromatic constituent enables spectroscopic (e.g., fluorescence) detection of the reaction product. Dansyl chloride also reacts with the i-amino group of lysine. The pK differences between α- and ε-amines can be exploited to modify one of these groups preferentially to the other.

Carbodiimides react with carboxyl groups to form an 0-acylisourea intermediate that is highly unstable in aqueous solution but can be stabilized through the addition of N-hydroxysuccinimide resulting in the formation of an acid stable intermediate that can be made to react with primary amines, producing an amide. The carboxyl terminus, glutamate and aspartate residues are all targets for carbodiimides in proteins at acidic pH (4.5–5). Carbodiimide chemistry is useful for labeling the C-terminus of protein. When carbodiimide chemistry is utilized, it is generally preferred that an excess of amine is added to the protein solution to inhibit crosslinking reactions. In another exemplary embodiment, a protein amine is labeled in a two-step process; an amine-containing fluorescent molecule is tethered to the protein through an N-hydroxysuccinimide intermediate of the protein or of a spacer arm attached to the protein.

Synthesis

Once the reactive group, linker, and ionizable groups have been selected, the final compound is synthesized by one of ordinary skill in the art utilizing standard organic chemistry reactions. A preferred compound for use within the present invention is PETMA-PITC, or an analogous agent. This compound retains the excellent characteristics of phenylisothiocyanate in the coupling. Furthermore, the compound performs well as a label in analytical methods because the electron structure of the phenyl ring is sufficiently separated from the quaternary ammonium group by the ethyl linker, thus allowing the isothiocyanate to react undisturbed by the quaternary ammonium group. Preparation of PETMA-PITC, C5 PETMA-PITC and PITC-311 are described in Aebersold et al., U.S. Pat. No. 5,534,440, issued Jul. 9, 1996.

With the selection of a suitable labeling moiety, conditions for attaching the label to the protein should ensure that the N- or C-terminus of the protein is uniformly labeled and that the labeled protein remains soluble in appropriate MS buffer systems. Typically, labeling will be carried out under denaturing conditions (e.g., surfactants or 8M urea). Surfactants and urea both suppress MS ionization and methods that provide rapid clean up and transfer of the labeled protein sample to a suitable MS buffer should also be employed.

Detectable Moieties

In another preferred embodiment, the protein is labeled with a moiety that enhances its detectability in, for example, protein purification and separation processes (e.g., electrophoresis). The detectable moiety can be detected by, for example, spectroscopy (e.g., UV/Vis, fluorescence, electron spin resonance (ESR), nuclear magnetic resonance (NMR) and the like), detection of radioactive isotopes, etc. When the protein is detected by UV/Vis, it is generally desirable to attach a chromophoric label to the protein (e.g., phenyl, napthyl, etc.). Similarly, for detection by fluorescence spectroscopy, a fluorophore is preferably attached to the protein. For ESR, the detectable moiety can be a free radical, such as a moiety including a nitroxide group. When the protein is detected by an NMR method, the detectable moiety can be enriched with an NMR accessible nuclei, such as fluorine, $^{13}C$, and the like.

In a presently preferred embodiment, the detectable moiety is a fluorophore. Many reactive fluorescent labels are commercially available from, for example, the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and PE-Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label.

There is a great deal of practical guidance available in the literature for selecting an appropriate fluorophore for a particular tag, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties, for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via readily available reactive groups that can be added to a molecule.

The diversity and utility of chemistries available for conjugating fluorophores to other molecules and surfaces is exemplified by the extensive body of literature on preparing nucleic acids derivatized with fluorophores. See, for example, Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a small molecular bioactive material, nucleic acid, peptide or other polymer.

In addition to fluorophores that are attached directly to a protein, the fluorophores can also be attached by indirect means. In an exemplary embodiment, a ligand molecule (e.g., biotin) is preferably covalently bound to the protein. The ligand then binds to another molecule (e.g., streptavidin), which is either inherently detectable or covalently bound to a signal system, such as a fluorescent compound of the invention, or an enzyme that produces a fluorescent compound by conversion of a non-fluorescent compound. Useful enzymes of interest as labels include, for example, hydrolases, particularly phosphatases, esterases and glycosidases, or oxidases, particularly peroxidases. Fluorescent compounds include fluorescein and its derivatives, rhodamine and its derivatives, dansyl, umbelliferone, etc., as discussed above. For a review of various labeling or signal producing systems that can be used, see, U.S. Pat. No. 4,391,904.

Presently preferred fluorophores of use in conjunction with the methods of the invention, include, for example, including fluoresceins, and rhodamine dyes. Many suitable forms of these compounds are widely available commercially with substituents on their phenyl moieties, which can be used as the bonding functionality for attachment of the fluorophore to a protein. Another group of preferred fluorescent compounds are the naphthylamines, having an amino group in the alpha or beta position. Included among such naphthylamino compounds are 1-dimethylaminonaphthy1-5-sulfonate, 1-anilino-8-naphthalene sulfonate and 2-p-toluidinyl-6-naphthalene sulfonate. Other donors include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

Useful fluorescent detectable moieties can be made to fluoresce by exciting them in any manner known in the art, including, for example, with light or electrochemical energy (see, for example, Kulmala et al, *Analytica Chimica Acta* 386: 1 (1999)). Means of detecting fluorescent labels are well known to those of skill in the art. Thus, for example, fluorescent labels can be detected by exciting the fluorophore with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product.

The fewer the processing steps between any separation technique and MS sequencing method, the faster that proteins can be identified, and the lower the cost of proteomic research. Typical electrophoresis buffers (e.g., Hochstrasser et al. *Anal Biochem.,* 173:424 (1988). and O'Farrel, *J Biol. Chem.,* 250:4007 (1975)) contain components (e.g., tris (hydroxymethyl)aminomethane buffers and sodium dodecyl sulfate, that supress the ionization of proteins in the mass spectrometer. These components may be replaced with other more volatile components (e.g., morpholinoalkylsulfonate buffers and ephemeral surfactants) that do not suppress ionization in the MS. In another embodiment, the samples are diluted with ammonium bicarbonate or ammonium acetate buffer to provide a volatile proton source for the mass spectrometer. Wilm, M. et al., *Anal. Chem.,* 68:1–8 (1996). In another embodiment, a buffer exchange is conducted through by chromatographic or tangential flow dialysis as the sample is transported from the outlet of the separation process to the inlet of the MS.

Labeling Procedure

In some instances, salts (e.g., TRIS and SDS) and urea present in electrophoresis buffers can suppress ionization of the labeled proteins and can generate small mass/charge ions that potentially confuse sequence analysis. Accordingly, spin dialysis procedures can be employed to rapidly exchange buffer systems prior to MS analysis. Alternatively, desalting columns (e.g., the ZipTip™ tip sold by Millipore) can be used for sample clean up and buffer exchange. Desalted samples can be resuspended in 0.1M ammonium bicarbonate as described by Wilm and Mann (see, Wilm, et al., ibid.) with minimal addition of methanol, or in 0.01M ammonium acetate buffer (with 0.1% formic acid) with minimal addition of acetonitrile as described by Mark (see "Protein structure and identification with MS/MS," paper presented at the PE/Sciex Seminar Series, Protein Characterization and Proteomics: Automated high throughput technologies for drug discovery, Foster City, Calif. (March, 1998)).

The coupling rates of the compound may be tested to ensure that the compound is suitable for sequencing polypeptides. In general, the faster the coupling rate the more preferred the compound. Coupling rates of between 2 and 10 minutes at 50° C. to 70° C. are particularly preferred. Similarly, fast reaction rates are also preferred, because exposure to the reaction mixture over an extended period of time might hydrolyze the peptide bonds, or lead to inefficient and irreproducible side reactions with the polypeptide residues, which could complicate mass spectral deconvolution.

In another preferred embodiment, one or more of the components of a protein mixture is reversibly attached to a solid support prior to the label being attached to a polypeptide. Various materials may be used as solid supports, including, for example, numerous resins, membranes or papers. These supports may additionally be derivatized to incorporate a cleavable functionality. A number of cleavable groups that may be used for this purpose include disulfides (—S—S—), glycol (—CH[OH]—CH[OH]—), azo (—N=N—), sulfone (—S[=O]—), and ester (—COO—) linkages (see, Tae, *Methods in Enzymology,* 91:580 (1983)). Supports which are particularly preferred include membranes such as Sequelon TM (Milligen/Biosearch, Burlington, Mass.). Representative materials for the construction of these supports include, among others, polystyrene, porous glass, polyvinylidinefluoride and polyacrylamide. In particular, polystyrene supports include, among others: (1) a (2-aminoethyl) aminomethyl polystyrene (see, Laursen, *J. Am. Chem. Soc.* 88: 5344 (1966)); (2) a polystyrene similar to number (1) with an aryl amino group (see, Laursen, *Eur. J. Biochem.* 20: 89 (1971)); (3) amino polystyrene (see, Laursen et al., *FEBS Lett.* 21: 67 (1972)); and (4)triethylenetetramine polystyrene (see, Hornet al., *FEBS Lett.* 36:285 (1973)). Porous glass supports include: (1) 3-aminopropyl glass (see, Wachter et al., *FEBS Lett.* 35: 97 (1973)); and (2)N-(2-aminoethyl)-3-aminopropyl glass (see, Bridgen, *FEBS Lett.* 50: 159 (1975)). Reaction of these derivatized porous glass supports with p-phenylene diisothiocyanate leads to activated isothiocyanato glasses (see, Wachter et al., supra). Polyacrylamide-based supports are also useful, including a cross-linked β-alanylhexamethylenediamine polydimethylacrylamide (see, Atherton et al., *FEBS Lett.* 64: 173 (1976)), and an N-aminoethyl polyacrylamide (see, Cavadore et al., *FEBS Lett.* 66: 155 (1976)).

One of ordinary skill in the art will readily utilize appropriate chemistry to couple the polypeptide to the solid supports described above (see, generally Machleidt and Wachter, Methods in Enzymology: [29] New Supports in Solid-Phase Sequencing 263–277 (1974). Preferred supports and coupling methods include the use of aminophenyl glass fiber paper with EDC coupling (see, Aebersold et al., *Anal. Biochem.* 187: 56–65 (1990)); DITC glass filters (see, Aebersold et al., *Biochem.* 27: 6860–6867 (1988) and the membrane polyvinylidinefluoride (PVDF) (Immobilon P TM, Milligen/Biosearch, Burlington, Mass.), along with SequeNet TM chemistry (see, Pappin et al., CURRENT RESEARCH IN PROTEIN CHEMISTRY, Villafranca J. (ed.), pp. 191–202, Academic Press, San Diego, 1990)).

In the practice of the present invention, attachment of the polypeptide to the solid support may occur by either covalent or non-covalent interaction between the polypeptide and solid support. For non-covalent attachment of the polypeptide to the solid support, the solid support is chosen such that the polypeptide attaches to the solid support by non-covalent interactions. For example, a glass fiber solid support may be coated with polybrene, a polymeric quaternary ammonium salt (see, Tarr et al., *Anal. Biochem.,* 84:622 (1978)), to provide a solid support surface which will non-covalently attach the polypeptide. Other suitable adsorptive solid phases are commercially available. For example, polypeptides in solution may be immobilized on synthetic polymers such as polyvinylidine difluoride (PVDF, Immobilon, Millipore Corp., Bedford, Mass.) or PVDF coated with a cationic surface (Immobilon CD, Millipore Corp., Bedford, Mass.). These supports may be used with or without polybrene. Alternatively, polypeptide samples can be prepared for sequencing by extraction of the polypeptide directly from polyacrylamide by a process called electroblotting. The electroblotting process eliminates the isolation of polypeptide from other peptides which may be present in solution. Suitable electroblotting membranes include Immobilon and Immobilon CD (Millipore Corp., Bedford, Mass.).

More recently, automated methods have been developed that allow chemistries to be performed on polypeptides immobilized on solid supports by non-covalent, hydrophobic interaction. In this approach, the samples in aqueous buffers, which may contain salts and denaturants, are pressure-loaded onto columns containing a solid support.

The bound polypeptide is then pressure-rinsed to remove interfering components, leaving the bound polypeptide ready for labeling (see, Hewlett-Packard Product Brochure 23-5091–5168E (November, 1992) and Horn, U.S. Pat. No. 5,918,273 (Jun. 29,1999).

The bound polypeptide is reacted under conditions and for a time sufficient for coupling to occur between the terminal amino acids of the polypeptide and the labeling moiety. The physical properties of the support may be selected to optimize the reaction conditions for a specific labeling moiety. For example, the strongly polar nature of the PETMA-PITC dictates covalent attachment of the polypeptide. Preferably, coupling with the amino groups of the polypeptide occurs under basic conditions, for example, in the presence of an organic base such as trimethylamine, or N-ethylmorpholine. In a preferred embodiment, the label is allowed to react with the bound peptide in the presence of 5% N-ethylmorpholine in methanol:water (75:25 v/v). Because of the mode of attachment, excess of reagent, coupling base and reaction by-products can be removed by very polar washing solvents prior to removal and sequencing of the labeled polypeptide by mass spectrometry. Various reagents are suitable as washing solvents, including, for example, methanol, water, mixtures of methanol and water, or acetone.

Less polar reagents, such as PITC-311, may be reacted with polypeptides attached to a sold support preferably by hydrophobic, non-covalent interactions. In this case, less polar washes are preferred, such as heptane, ethylacetate, and chloroform. Following the washing cycle, the labeled polypeptide is dissociated from the solid support by elution with solvent containing 50% to 80% of aqueous methanol or acetonitrile.

When the labeling reaction is conducted entirely in solution phase, the reaction mixture is preferably submitted to a purification cycle, such as dialysis, gel permeation chromatography, and the like.

In another aspect, the present invention provides a method for sequencing a portion of a protein in a protein mixture, the method comprising:

(a) contacting the protein mixture with a C-terminus or N-terminus labeling moiety to covalently attach a label to the C- or N-terminus of the protein and form a labeled protein mixture;

(b) separating individual labeled proteins in the protein mixture; and (c) analyzing the labeled proteins from step (b) by a mass spectrometric method to determine the sequence of at least two C-terminus or two N-terminus residues.

In one group of embodiments, the method further comprises:

(d) identifying the protein by using the sequence of at least two C-terminus or two N-terminus residues in combination with a separation coordinate of the labeled protein and the protein terminus location of the sequence to search predicted protein sequences from a database of gene sequence data.

Separation

In a preferred embodiment, the tagging procedure is performed on a mixture of proteins. Following the tagging procedure the mixture of proteins is submitted to a separation process, which preferably allows the separation of the protein mixture into discrete fractions. Each fraction is preferably substantially enriched in only one labeled protein of the protein mixture.

The methods of the present invention are utilized in order to determine the sequence of a polypeptide. Within preferred embodiments of the invention, the polypeptide is "substantially pure," which means that the polypeptide is about 80% homogeneous, and preferably about 99% or greater homogeneous. Many methods well known to those of ordinary skill in the art may be utilized to purify the polypeptide prior to determining its amino acid sequence. Representative examples include HPLC, Reverse Phase-High Pressure Liquid Chromatography (RP-HPLC), gel electrophoresis, chromatography, or any of a number of peptide purification methods (see, generally the series of volumes entitled METHODS IN PROTEIN SEQUENCE ANALYSIS).

Even more preferred is the use of capillary electrophoresis and particularly, multi-dimensional capillary electrophoresis, such as that described in the commonly assigned co-pending U.S. patent application Ser. No. 09/513486, titled "Protein Separation via Multidimensional Electrophoresis," and filed on an even date herewith.

Although substantially pure polypeptides are preferably utilized within the methods described herein, it is also possible to determine the sequence of polypeptide mixtures. Briefly, in one embodiment, an algorithm is utilized in order to determine all of the hypothetical sequences with a calculated mass equal to the observed mass of one of the peptides in the mixture. See, Johnson et al., *Protein Science* 1:1083–1091 (1992). These sequences are then assigned figures of merit according to how well each of them accounts for the fragment ions in the tandem mass spectrum of the peptide utilizing such algorithms, the sequence of polypeptides within the mixture may be readily determined.

As described above, the methods herein are particularly useful for identifying proteins from a healthy or diseased tissue sample. In one group of embodiments, the methods are applied to both a mixture of proteins from a healthy tissue sample and a mixture of proteins from a diseased tissue sample. Accordingly, the protein mixtures used in this aspect of the invention can be obtained from essentially any source. Methods of isolating proteins from tissue samples are well known.

Within the present invention, the polypeptide with a derivatized terminal amino acid is sequenced by a mass spectrometer. Various mass spectrometers may be used within the present invention. Representative examples include, triple quadrupole mass spectrometers, magnetic sector instruments (magnetic tandem mass spectrometer, JEOL, Peabody, Mass.); ion-spray mass spectrometers, Bruins et al., *Anal. Chem.* 59: 2642–2647 (1987); electrospray mass spectrometers, Fenn et al., *Science* 246: 64–71 (1989); laser desorption time-of-flight mass spectrometers, Karas et al., *Anal. Chem.* 60: 2299–2301 (1988), and a Fourier Transform Ion Cyclotron Resonance Mass Spectrometer (Extrel Corp., Pittsburgh, Mass.). Within a preferred embodiment, an electrospray mass spectrometer (Mariner™ model, PE Biosystems, Foster City, Calif.) is utilized to fragment the derivatized terminal polypeptide, and a time-of-flight detector with better than 50 ppm mass accuracy is used to determine the sequence from the masses of the labeled fragments.

One of skill in the art will appreciate that the sequence information obtained using the methods of the invention can be combined with other characteristics of the protein under analysis to even further reduce the number possible identities of the protein. Thus, in a preferred embodiment, the method of the invention combines information from a protein sequence tag with one or more other protein characteristics to identify the protein. Data that are useful to supplement the sequence data include, but are not limited to, amino acid composition, the number and identity of specific residues (e.g. cysteine), cleavage information, proteolytic (e.g., tryptic) and or chemolytic peptide mass, subcellular location, and separation coordinates (e.g., retention time, pI, 2-D electrophoresis coordinates, etc.). Other forms of data characteristic of a particular protein or class of proteins that can be combined with information from the PSTs of the invention to identify a protein will be apparent to those of skill in the art. As the body of data characteristic of a particular protein becomes more comprehensive, proteins under analysis can be identified using shorter protein sequence tags.

Thus, in a further preferred embodiment, information regarding one or more characteristics of a protein is combined with information from a PST of about 4 amino acids in length, more preferably about 3 amino acids in length, more preferably still, about 2 amino acids in length is used to identify the protein.

The materials, methods and devices of the present invention are further illustrated by the examples which follow. These examples are offered to illustrate, but not to limit the claimed invention.

EXAMPLES

Example 1 illustrates the use of inverted mass ladder sequencing to determine the sequence of glycogen phosphorylase.

Example 2 illustrates the use of inverted mass ladder sequencing to determine the sequence of bradykinin labeled with phenylisothiocyanate.

Example 3 illustrates the use of inverted mass ladder sequencing to determine the sequence of bradykinin labeled with iminobiotin.

Example 4 illustrates the application of inverted mass ladder sequencing using a 4-sulfophenylisothiocyanate-labeled apomyoglobin.

Example 5 illustrates the use of inverted mass ladder sequencing to determine the sequence of bradykinin labeled at the carboxy-terminus (C-terminus) with (2-aminoethyl) trimethylammonium chloride hydrochloride (2-AETA) via 1-ethyl-3-(3-dimethylaminopropyl)-carbodiimide hydrochloride (EDC).

Example 6 illustrates the utility of inverted mass ladder sequencing for the identification of the protein glycogen phosphorylase a by searching a genomics database for matching protein sequence tags (PST) and limiting that search based on the position of the PST in the protein sequence.

Example 7 illustrates the utility of inverted mass ladder sequencing for the identification of the human peptide Bradykinin by searching a genomics database for matching protein sequence tags (PST) and limiting that search based on the position of the PST in the protein sequence and separation coordinates.

Example 8 illustrates the utility of inverted mass ladder sequencing for the identification of the horse apomyoglobin protein by searching a genomics database for matching protein sequence tags (PST) and limiting that search based on the position of the PST in the protein sequence and separation coordinates of the protein.

Example 1

This example illustrates the use of inverted mass ladder sequencing to determine the sequence of glycogen phosphorylase.

Glycogen phosphorylase A (EC 2.4.1.1) is a member of a group of proteins that are acetylated at the amino-terminus (see, Persson et al., *Eur. J. Biochem.* 152: 523–527(1985)). This acetyl group can be attached to the N-terminus via natural biochemical means, as is the case in glycogen phosphorylase. N-terminal acetylation can also be accomplished through published protocols (see, Lomant et al., *J. Mol. Biol.*, 104: 243–261 (1976)) using N-hydroxysuccimidyl- or sulfo-N-hydroxysuccimidyl-acetate, which are commercially available (Pierce Chemical Co., Rockford, Ill.). This acetyl group provides a unique mass signature for inverted mass ladder sequence determination.

Acetylated glycogen phosphorylase A was purchased from Sigma-Aldrich Chemical Co. (Catalog # P1261). The protein was dissolved in 4 mM ammonium acetate buffer (pH=5.0) at 0.72 mg/mL. This sample (500 $\mu$L) was purified of residual nonvolatile ions and low molecular weight protein and peptide impurities by dialysis using a Microcon (Millipore Corporation) spin dialysis tube with a 50,000 MW cutoff membrane. The sample was dialyzed 10 times against the 4 mM ammonium acetate buffer following Microcon product instructions. The retentate was recovered in 460 $\mu$L of the ammonium acetate buffer, yielding a final protein concentration of about 0.8 mg/mL.

The recovered retentate was subjected to in-source fragmentation in an electrospray-time-of-flight mass spectrometer—a Mariner™ (PE Biosystems, Inc.) equipped with the commercial Microspray ion source. The mass spectrometer settings were optimized and the instrument was calibrated immediately prior to injecting the glycogen phosphorylase sample according to the published instrument protocols. The sample was fed continuously into the microspray source at a rate of 0.4 $\mu$L/min. The nozzle potential was increased from the minimum setting of 12 V to a maximum of 350 V in 25 V increments with 5 minutes instrument equilibration time alotted before collecting spectra at each nozzle potential. A total of thirty 3-second spectra were accumulated for analysis at each nozzle potential.

The identity and purity of the parent glycogen phosphorylase A protein was determined at the minimally fragmenting 12 V spectrum (FIG. 1) by conducting a zero charge mass deconvolution of the multiply charged mass peaks observed between 700 and 4000 amu using the BioSpec Data Explorer™ software (Version 3.0) supplied by the vendor. The N-terminal sequence of glycogen phosphorylase was determined by inspecting the resulting mass spectra to determine the relative abundance of the possible acetylated peptides at each nozzle potential. Peaks corresponding to the acetylated peptide masses were clearly observed to increase in relative abundance with increasing nozzle potential (FIG. 2). FIG. 2 shows the cumulative relative abundance of both the a- and b-ions for each peptide mass in the sequence. An example of a substantially fragmented mass spectrum, corresponding to 250V nozzle potential is shown in FIG. 3. Those mass fragments showing increased abundance at nozzle potentials above 200V correspond to the published amino-terminal sequence for glycogen phosphorylase, acetyl-SRPLSD (see, Persson et al., ibid).

The lack of a ionizable residue on either the amino-terminal serine or the acetate label prevented direct detection of the first amino acid in the sequence. However, the identity of this amino acid is readily deduced from the cumulative mass of the second peptide fragment (corresponding to acetyl-SR), which creates the first detectable positively charged ion from the R-residue. The sequence of the peptide mass ladder became ambiguous beyond the sixth amino acid residue at all nozzle potentials tested.

Example 2

This example illustrates the use of inverted mass ladder sequencing to determine the sequence of bradykinin labeled with phenylisothiocyanate.

Bradykinin, a 9 amino acid peptide, was purchased from Sigma-Aldrich (Cat # B3259) and used as supplied. Bradykinin (5 mmoles) was solubilized in 100 µL of coupling buffer consisting of 10 µL of triethylamine (neat), 10 µL of 2 M acetic acid, 5 µL of sequencing grade phenylisothiocyanate (PITC) purchased from Pierce (Cat # 26422), and 2 mL of 50% aqueous methanol. The coupling mixture was incubated for 10 min at 55° C. The reaction mixture was cooled to room temperature and extracted twice with 150 µL of a 2:1 (v/v) heptane/ethyl acetate solution. The extracted aqueous phase was lyophilized and resuspended to 2 µM PITC-bradykinin in a 50% aqueous acetonitrile solution containing 1% by volume acetic acid.

The PITC-labeled Bradykinin was subjected to in-source fragmentation in an electrospray-time-of-flight mass spectrometer-a Mariner™ (PE Biosystems, Inc.) equipped with the standard commercial pneumatic electrospray ion source. The mass spectrometer settings were optimized and the instrument was calibrated immediately prior to injecting the PITC-Bradykinin sample according to the published instrument protocols. The sample was fed continuously into the electrospray source at a rate of 5 µL/min. The nozzle potential was increased from the minimum setting of 12 V to a maximum of 350 V in 25 V increments with 1 minute of instrument equilibration time alotted before collecting spectra at each nozzle potential. A total of thirty 3-second spectra were accumulated for analysis at each nozzle potential.

The identity and purity of the parent PITC-Bradykinin peptide was determined at the minimally fragmenting 12 V spectrum (FIG. 4) based on the calculated mass for the expected reaction product. The concentration of residual unlabeled Bradykinin was determined by standard addition to be less than 5%. The N-terminal sequence of Bradykinin was determined by inspecting the resulting mass spectra to determine the relative abundance of the possible PITC-labeled peptide fragments at each nozzle potential. Peaks corresponding to the PITC-labeled peptide masses were clearly observed to increase in relative abundance with increasing nozzle potential (FIG. 5). FIG. 5 shows the cumulative relative abundance of the sum of the a- and b-ions for each peptide mass in the sequence. An example of a substantially-fragmented mass spectra, corresponding to a nozzle potential of 250 V is shown in FIG. 6. Those mass fragments showing increased abundance at nozzle potentials above 200V correspond to the published amino-terminal sequence for Bradykinin (see, Sigma Product Catalog, Biochemicals and Reagents for Life Science Research, 1999).

Some of the PITC-Bradykinin fragments are seen to overlap the peaks of other ions produced by the sample matrix. The $b_1$-ion (PITC-R) overlapped the first monoisotopic peak of an ion identified as being produced from the sample matrix (in the absence of labeled Bradykinin). The abundance of this matrix ion was found to remain invariant with nozzle potential. Similarly, the $a_2$-ion peak (PITC-RP) was found to overlap the second isotope peak of another ion produced by the matrix. In this case the matrix ion was found to disappear with increasing nozzle potential. The expected relative abundance of the first through third isotope species and inspection of both the a- and b-ion positions were used to determine and deconvolute these overlaps in the mass spectra as previously described (see, Hines et al., *Am. Soc. Mass. Spec.* 3: 326–336 (1992)).

Example 3

This example illustrates the use of inverted mass ladder sequencing to determine the sequence of bradykinin labeled with iminobiotin.

Bradykinin was purchased from Sigma-Aldrich (Cat # B3259) and used as supplied. The N-hydroxysuccimidyl (NHS) ester of iminobiotin was purchased from Pierce (Cat #21117ZZ) and used as supplied. Bradykinin (5 nmoles) was dissolved in 100 µL of 1 M pyridinium acetate buffer (pH 8.0). The NHS-iminobiotin was dissolved in DMSO to a final concentration of 6.25 mg/mL with 3.5 µL of this DMSO solution added to the reaction mixture. The reaction mixture was incubated for 2 h at 4° C. The sample was lyophilized and resuspended to final iminobiotin (IMB)-labeled Bradykinin concentration of 2 µM in a 50% aqueous acetonitrile solution containing 1% by volume acetic acid.

The iminobiotin (IMB)-labeled Bradykinin was subjected to in-source fragmentation in an electrospray-time-of-flight mass spectrometer—a Mariner™ (PE Biosystems, Inc.) equipped with the standard commercial pneumatic electrospray ion source. The mass spectrometer settings were optimized and the instrument was calibrated immediately prior to injecting the PITC-Bradykinin sample according to the published instrument protocols. The sample was fed continuously into the electrospray source at a rate of 5 µl/min. The nozzle potential was increased from a minimum setting of 75 V to a maximum of 400 V in 25 V increments with 1 minute of instrument equilibration time alotted before collecting spectra at each nozzle potential. A total of thirty 3-second spectra were accumulated for analysis at each nozzle potential.

The identity and purity of the parent IMB-Bradykinin peptide was determined at the minimally fragmenting 75 V spectrum based on the calculated mass for the expected reaction product. The concentration of residual unlabeled Bradykinin was determined by standard addition to be less than 5%. The N-terminal sequence of Bradykinin was determined by inspecting the resulting mass spectra to determine the relative abundance of the possible IMB-labeled peptide fragments at each nozzle potential. Peak counts corresponding to the a-ions (FIG. 7) and b-ions (FIG. 8) generated from the IMB-labeled peptide fragment masses were clearly observed to increase in relative abundance with increasing nozzle potential with a maximum fragmentation abundance noted at about 200V. The decrease in fragment ion abundance above 200V is attributed to an overall decline in detection or ionization efficiency of all iminobiotin species and parallels the observed decline in total counts (FIG. 7 and FIG. 8). Those mass fragments showing an increased abundance at the 200V nozzle potential correspond to the published amino-terminal sequence for Bradykinin.

Example 4

This example illustrates the application of inverted mass ladder sequencing using a 4-sulfophenylisothiocyanate-labeled apomyoglobin.

Sequencing grade apomyoglobin was purchased from Sigma-Aldrich (Cat #A8673) and used as supplied. Apomyoglobin (10 nmoles) was dissolved in 100 µL of reaction buffer consisting of: 10 µL of triethylamine, 10 µL of 2 M acetic acid, 2 mL of 8 M urea. A quantity of 10 µL of a 10 mg/mL aqueous 4-sulfophenylisothiocyanate (SPITC) was added to this solution. SPITC was purchased from Fluka (Cat # 86180) and used as supplied. The reaction mixture was incubated for 1 h at 55° C. Urea and excess reagents were removed from the reaction mixture by spin dialysis against 6 washes with deionized water. Spin dialysis was conducted in a model YM10 Microcon (Millipore Cat# 42407) tube following package directions. The dialyzed sample was lyophilized and resuspended in 500 µL of 50% aqueous acetonitrile containing 0.1% by volume triethylamine.

The SPITC-labeled apomyoglobin sample was subjected to in-source fragmentation in an electrospray-time-of-flight mass spectrometer-a Mariner™ (PE Biosystems, Inc.) equipped with the standard commercial pneumatic electrospray ion source. The mass spectrometer was operated in negative ion mode. The mass spectrometer settings were optimized and the instrument was calibrated immediately prior to injecting the sample according to the published instrument protocols. The sample was fed continuously into the electrospray source at a rate of 3 µl/min. The nozzle potential was increased from a minimum setting of 125 V to a maximum of 300V in 25–50 V increments (FIG. 9) with 1 minute of instrument equilibration time alotted before collecting spectra at each nozzle potential. A total of thirty 3-second spectra were accumulated for analysis at each nozzle potential.

Significant amounts of the SPITC label were found to detach from the protein and fragment ions at higher nozzle potentials (FIG. 9), inhibiting the sensitivity of this label for sequence determination. However, peaks corresponding to the fragment masses of the first 3 amino acid residues of the apomyoglobin protein (sequence from Genbank) were found to increase in abundance at higher nozzle potentials. The labeled $a_1$-ion fragment appears at nozzle potentials above 200V. The $b_1$, $a_2$, $b_2$, $a_3$, and $b_3$ ions all appear to increase in relative abundance only above nozzle potentials of 250V (FIG. 10).

Example 5

This example illustrates the use of inverted mass ladder sequencing to determine the sequence of bradykinin labeled at the carboxy-terminus (C-terminus) with (2-aminoethyl) trimethylammonium chloride hydrochloride (2-AETA) via 1-ethyl-3-(3-dimethylaminopropyl)-carbodiimide hydrochloride (EDC).

Bradykinin (Cat # B3259), 2-AETA (Cat # 284556), and 2-[N-Morpholino]ethanesulfonic acid (MES) (Cat # M5287) were purchased from Sigma-Aldrich and used as supplied. EDC was purchased from Pierce (Cat # 22980) and used as supplied. Bradykinin (0.67 µmol) was dissolved in 0.25 mL 0.1 M MES buffer (pH 5.0). This solution was added to 8.0 µmol 2-AETA, and the solution was mixed until the solid was dissolved. This solution was then added to 37.5 µmol EDC and thoroughly mixed until the EDC was dissolved. The sample was incubated at ambient temperature overnight.

A sample was prepared for mass spectrometry by diluting the reaction mixture in a 50% aqueous acetonitrile solution containing 1% by volume acetic acid such that the final concentration of 2-AETA-labeled bradykinin was 10 µM. The 2-AETA-labeled bradykinin was subjected to in-source fragmentation in an electrospray-time-of-flight mass spectrometer—a Mariner™ (PE Biosystems, Inc.) equipped with the standard commercial pneumatic electrospray ion source. The mass spectrometer settings were optimized and the instrument was calibrated immediately prior to injecting the 2-AETA-labeled bradykinin sample according to the manufacturer's instrument protocols. The sample was infused continuously into the electrospray source at a rate of 5 µL/min. The nozzle potential was increased from a minimum setting of 50 V to a maximum of 300 V in 50 V increments with 1 minute of instrument equilibration time alotted before collecting spectra at each nozzle potential.

Data in the range of 50–2000 mass-to-charge units were captured in each spectrum, and a total of sixty 3-second spectra were accumulated for analysis at each nozzle potential.

The identity of the parent 2-AETA-labeled bradykinin was determined at the minimally fragmenting 50-V spectrum based on the calculated mass for the expected reaction product. The C-terminal sequence of bradykinin was determined by inspecting the resulting mass spectra to determine the relative abundance of the possible 2-AETA-labeled peptide fragments at each nozzle potential. Peak counts corresponding to the entire possible series of $y^{+2}$ ions (FIG. 11) generated from the 2-AETA-labeled peptide fragment masses were clearly observed to increase in relative abundance with increasing nozzle potential with a maximum fragmentation abundance in the region of 150–200 V. With this label, which carries a fixed positive charge, no singly-charged y ions were observed since the C-terminal residue of bradykinin is arginine. Those mass fragments showing an increased abundance in the range of 150–200 V nozzle potential correspond to the published C-terminal sequence for bradykinin.

Example 6

This example illustrates the utility of inverted mass ladder sequencing for the identification of the protein glycogen phosphorylase a by searching a genomics database for matching protein sequence tags (PST) and limiting that search based on the position of the PST in the protein sequence.

The deduced N-terminal amino acid sequence of glycogen phosphorylase A from Example 1 (i.e., SRPLSD) was used to search the SWIS-PROT and TrEMBEL protein sequence databases using the published ExPASy TagIdent tool (see, http://www.expasy.ch/tools/tagident.html). This tool enables searching known protein sequences contained within the database for any that contain matching sequences to a 1–6 continguous amino acid PST. The search can be limited by the position of the PST in the protein (i.e., N-terminal or C-terminal) and the use of the electrophoretic coordinates isoelectric point and/or apparent molecular weight.

The search was limited to the 490 rabbit protein sequences contained within the database at the time. The number of matching proteins ("hits") were found to decrease with increasing PST length (Table 2). The number of hits at any given PST length could be further reduced by limiting the search further to N-terminal matches (Table 2). The number of hits at any given PST length are also reduced (Table 2) by including the apparent MW of the protein (100+/−20 kDa), determined from a capillary gel electrophoretic separation.

TABLE 2

Glycogen Phosphorylase Identification from a Genomic Database using an N-terminal IMLS PST

| PST | Number of hits based on PST | Number of N-terminal hits | Number of N-terminal hits limited by MW |
|---|---|---|---|
| S | 478 | 22 | 1 |
| SR | 299 | 1 | 1 |
| SRP | 1 | 1 | 1 |

Example 7

This example illustrates the utility of inverted mass ladder sequencing for the identification of the human peptide Bradykinin by searching a genomics database for matching protein sequence tags (PST) and limiting that search based on the position of the PST in the protein sequence and separation coordinates.

The deduced N-terminal amino acid sequence of bradykinin determined from Examples 2 and 3 (i.e., RPPGFS) was used to search the SWIS-PROT and TrEMBEL protein sequence databases as described in Example 6.

The search was limited to the 7171 human protein sequences contained within the database at the time. The number of matching proteins ("hits") were found to decrease with increasing PST length (Table 3). The number of hits at any given PST length could be further reduced by limiting the search further to N-terminal matches (Table 3). The number of hits at any given PST length were also reduced (Table 3) by including the apparent MW of the peptide (1000+/−200 Da), determined from the zero charge mass of the parent peptide in an ESI-TOF MS.

TABLE 3

Human Bradykinin Identification from a
Genomic Database using an N-terminal IMLS PST

| PST | Number of hits based on PST | Number of N-terminal hits | Number of N-terminal hits limited by MW |
|---|---|---|---|
| RP | 4114 | 13 | 1 |
| RPP | 638 | 4 | 1 |
| RPPG | 66 | 1 | 1 |
| RPPGF | 5 | 1 | 1 |
| RPPGFS | 3 | 1 | 1 |

Example 8

This example illustrates the utility of inverted mass ladder sequencing for the identification of the horse apomyoglobin protein by searching a genomics database for matching protein sequence tags (PST) and limiting that search based on the position of the PST in the protein sequence and separation coordinates of the protein.

The deduced N-terminal amino acid sequence of apomyoglobin was determined from Example 4 (i.e., GLS) was used to search the SWIS-PROT and TrEMBEL protein sequence databases as described in Example 6.

The search was limited to the 241 horse protein sequences contained within the database at the time. The number of matching proteins ("hits") were found to decrease with increasing PST length (Table 4). The number of hits at any given PST length could be further reduced by limiting the search further to N-terminal matches (Table 4). The number of hits at any given PST length were also reduced (Table 4) by including the apparent MW of the protein (17+/−3.4 kDa), determined from the zero charge mass of the parent protein in an ESI-TOF MS, and the isoelectric point of the protein (pI=7+/−0.5) determined by capillary isoelectric focusing.

TABLE 4

Horse Apomyoglobin Identification from a
Genomic Database using an N-terminal IMLS PST

| PST | Number of hits based on PST | Number of N-terminal hits | Number of N-terminal hits limited by MW | Number of N-terminal hits Limited by pI and MW |
|---|---|---|---|---|
| G | 235 | 10 | 5 | 1 |
| GL | 148 | 2 | 1 | 1 |
| GLS | 29 | 1 | 1 | 1 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for sequencing a portion of a protein in a protein mixture, said method comprising:
    (a) contacting said protein mixture with a C-terminus or N-terminus labeling moiety comprising a mixture of at least two isotopically distinct chemical species to covalently attach a label to the C- or N-terminus of said protein and form a labeled protein mixture;
    (b) separating individual labeled proteins in said protein mixture; and
    (c) analyzing said labeled proteins from step (b) by a mass spectrometric method to determine the sequence of at least two C-terminus or two N-terminus residues.

2. A method in accordance with claim 1, further comprising a step prior to step (a) of isolating a group of proteins from a cell extract.

3. A method in accordance with claim 2, wherein said cell extract is from a diseased tissue sample.

4. A method in accordance with claim 2, wherein said cell extract is from a healthy tissue sample.

5. A method in accordance with claim 1, wherein said separating is conducted by electrophoresis of the labeled protein mixture.

6. A method in accordance with claim 1, wherein said separating is conducted by at least one method of capillary electrophoresis of the labeled protein mixture.

7. A method in accordance with claim 6, wherein said mass spectrometric method uses ESI-TOF MS.

8. A method in accordance with claim 1, wherein said mass spectrometric method uses ESI-TOF MS.

9. A method in accordance with claim 1, further comprising:
    (d) identifying said protein by using said sequence of at least two C-terminus or two N-terminus residues in combination with a separation coordinate of said labeled protein and the protein terminus location of said sequence to search predicted protein sequences from a database of gene sequence data.

10. The method according to claim 1, wherein said labeling moiety comprises a member selected from the group of a mixture of $^{12}C$ and $^{13}C$; a mixture of $^{14}N$ and $^{15}N$; a mixture of $^{16}O$ and $^{18}O$; a mixture of $^{35}Cl$ and $^{37}Cl$; a mixture of $^{79}Br$ and $^{81}Br$; a mixture of $^{1}H$ and $^{2}H$ and combinations thereof.

* * * * *